United States Patent
Berg-Schultz et al.

(10) Patent No.: US 7,897,779 B2
(45) Date of Patent: Mar. 1, 2011

(54) IONIC UV-A SUNSCREENS AND COMPOSITIONS CONTAINING THEM

(75) Inventors: Katja Berg-Schultz, Kaiseraugst (CH); Ulrich Huber, Erlenbach (CH); Daniel Sprenger, Basel (CH)

(73) Assignee: DSM IP Assets B.V., TE Heerlen (NL)

( * ) Notice: Subject to any disclaimer, the term of this patent is extended or adjusted under 35 U.S.C. 154(b) by 0 days.

(21) Appl. No.: 10/589,051

(22) PCT Filed: Feb. 11, 2005

(86) PCT No.: PCT/EP2005/001379

§ 371 (c)(1), (2), (4) Date: Mar. 26, 2007

(87) PCT Pub. No.: WO2005/080341

PCT Pub. Date: Sep. 1, 2005

(65) Prior Publication Data

US 2007/0275090 A1    Nov. 29, 2007

(30) Foreign Application Priority Data

Feb. 13, 2004   (EP) ................................. 04003294

(51) Int. Cl.
- *C07D 213/00* (2006.01)
- *C07F 9/06* (2006.01)
- *A61K 33/24* (2006.01)
- *A61K 33/14* (2006.01)

(52) U.S. Cl. ................. 546/332; 546/339; 546/22; 424/617; 424/663; 424/669; 424/677; 424/678; 424/679; 424/680; 424/681

(58) Field of Classification Search ................. 546/332, 546/339; 424/677, 678, 679, 680, 681
See application file for complete search history.

(56) References Cited

U.S. PATENT DOCUMENTS

| 5,321,130 A | 6/1994 | Yue et al. |
| 5,734,058 A | 3/1998 | Lee |
| 7,611,696 B2 * | 11/2009 | Berg-Schultz ............... 424/59 |
| 2005/0019278 A1 * | 1/2005 | Berg-Schultz ............... 424/59 |

FOREIGN PATENT DOCUMENTS

| EP | 1 362 894 A2 | 11/2003 |
| WO | WO 95/01341 A1 | 1/1995 |
| WO | WO 03/068183 A1 | 8/2003 |

OTHER PUBLICATIONS

Tanaka et al Bull. Chem. Soc. Jpn. 1984, 57, 2198-2202.*
F. Zaragoza Dörwald"Side Reactions in Organic Synthesis: A Guide to Successful Synthesis Design" 2005 Wiley-VCH Verlag GmbH & Co. KGaA, Weinheim.*
Hawley's Condensed Chemical Dictionary 14$^{th}$, 2001, John Wiley & Sons, Inc., New York, p. 613.*
Basin et al Organic Process Research and Development 2000, 4, 427-435.*
Boyd et al Journal of the Chemical Society, Section C, Organic 1967, 19, 1866-1868.*
Van Allan et al Journal of Chemical and Engineering Data 1977, 22, 101-104.*
Van Allan et al Journal of Heterocyclic Chemistry 1971, 8, 367-371.*
Urayama et al., "New Organic Conductors Based On AzaTCNQ," *Synthetic Metals*, vol. 19, pp. 469-474, XP-002327953 (1987).
Matsubayashi et al., "Preparation and Properties of AzaTCNQ-Anion Salts and Mixed AzaTCNQ-/ TCNQ-/TCNQ Salts of some Tetrakis(isocyanide)rhodium(I) Cation, and X-Ray Crystal Structure of the AzaTCNQ—Tetrakis(2,6-dimethylphenyl-isocyanide)rhodium(I)+ Salt," *Inorganica Chimica Acta*, vol. 63, pp. 217-224, XP-002327952 (1982).

* cited by examiner

*Primary Examiner*—Rita J Desai
*Assistant Examiner*—John Mabry
(74) *Attorney, Agent, or Firm*—Bryan Cave LLP

(57) ABSTRACT

The present invention relates to novel 1,4-dihydropyridine derivatives, to novel cosmetic or dermatological sunscreen compositions containing these derivatives and the use of these derivatives for photoprotecting human skin and/or hair against UV radiation, in particular solar radiation.

2 Claims, No Drawings

IONIC UV-A SUNSCREENS AND COMPOSITIONS CONTAINING THEM

The present invention relates to novel 1,4-dihydropyridine derivatives, to novel cosmetic or dermatological sunscreen compositions containing these derivatives and the use of these derivatives for photoprotecting human skin and/or hair against UV radiation, in particular solar radiation.

There is a constantly increasing need for sunscreen protection agents in a population which is exposed to an increasing amount of damaging sunlight. Repetitive sun exposure can result in skin changes known as photoaged skin. The clinical changes that are seen in photoaged skin differ from those of normally aged skin in the sunlighted protected sites of the body. Among damaging results of extensive sun exposure of the skin there is increased wrinkling, elastosis, pigmentary changes, precancerous and cancerous skin lesions.

Many sunscreen chemicals have been developed in the past protecting against the harmful effect of UV-A (320 to 400 nm) and/or UV-B (290 to 320 nm) wavelength and even shorter wavelength (UV-C). These chemicals are usually incorporated either alone or in combination with each other into cosmetic or pharmaceutical preparations which are widely known and used.

In particular UV-A radiation causes a rapid, weak direct pigmentation of the skin. UV-A rays penetrate into deeper skin layers and there can accelerate the ageing process of the skin. The shorter wave UV-A II radiation assist the formation of sunburn. The UV-A radiation can furthermore cause phototonic or photoallergic skin reactions. There is a relationship between UV-A exposure and increased risk of skin cancer.

While there exists a large number of safe and effective UV-B absorbers, the number of UV-A absorbers suitable for the protection of human skin is rather restricted. A good UV-A absorber should have excellent photostability, toxicological and dermatological acceptability, excellent heat stability, very good solubility in cosmetic solvents, in particular in oil or water, compatibility with cosmetic bases, pH stability in the range of 4 to 9, processability into cosmetic formulations, compatibility with other ingredients of cosmetic formulations and with the packaging materials, no staining of textiles, it should be free of color and of neutral or pleasant odor, and it should be free of tackiness and have a low volatility. In particular for application to hair such as in hairsprays, shampoos, hair care products, etc., high requirements must be met, and the UV-absorber must adhere to the hair to provide sufficient protection.

Oil-soluble sunscreens which absorb in the UV-A range are disclosed e.g. in WO 03/068183.

While the number of available UV-A absorbers which meet at least some of the above requirements is already short, the number of UV-A absorbers which are hydrosoluble or which are suitable for application to the hair is even shorter. A hydrosoluble UV-A sunscreen has the advantage that it can be incorporated into the water phase of usual oil-in-water or water-in-oil emulsions. Since usually in those emulsions there is more water phase than oil phase, more sunscreen can be incorporated into the water phase than into the oil phase, which leads to compositions having a higher sunprotection factor. Furthermore, water-soluble UV-A sunscreens could be combined with known oil-soluble UV-A sunscreens in the oil phase of a two-phase emulsion, which again leads to an increase of the sunprotection factor.

Water-soluble UV-A sunscreens are disclosed e.g. in EP-A 669 323 which discloses both water-soluble and oil-soluble sunscreens. However, the water-soluble UV-A sunscreens disclosed in this document, e.g. the compound disodium phenyldibenzimidazole tetrasulfonate have an absorption maximum at 335 nm and an extinction value E of only 745, which is relatively low. An absorption maximum between 350 to 370 nm would be preferable. Furthermore, it would be preferable to have UV-A sunscreens which are water-soluble and/or which advantageously adhere to hair which have a higher extinction E, which would improve the efficiency of the sunscreen. E values of more than 900, preferably more than 1000, e.g. 1000 to 1200, would be very advantageous.

UV-A sunscreens are also disclosed in DE 33 24 735, and some of the sunscreens disclosed in this document are also water-soluble. An example of such a water-soluble UV-A sunscreen is terephthalylidene dicamphorsulfonic acid, however, this compound has an extinction coefficient E of only 866, and the absorption maximum is at 345 nm.

There still exists the need for further UV-A sunscreens which are water-soluble and/or adhere to hair which do not only meet the requirement for sunscreens as indicated above but which also have an absorption maximum at rather high wavelength, preferably between about 350 to 370 nm, and have excellent E values, preferably 900 or more, more preferably 1000 or more.

This object is achieved by compounds of the general formula (I)

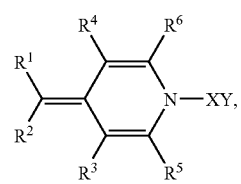

wherein
$R^1$ and $R^2$ are identical or different electron-withdrawing groups or one of $R^1$ and $R^2$ is hydrogen and the other of $R^1$ and $R^2$ is an electron-withdrawing group,
$R^3$, $R^4$, $R^5$ and $R^6$ are independently selected from hydrogen atoms, $C_1$-$C_{10}$ alkyl groups, $C_2$-$C_{10}$ alkenyl groups, $C_2$-$C_{10}$ alkynyl groups, $C_3$-$C_{10}$ cycloalkyl groups, $C_6$-$C_{10}$ aryl groups, the above groups being unsubstituted or optionally substituted by one to three substituents selected from $C_1$-$C_6$ alkyl groups, halogen, hydroxy and $C_1$-$C_6$ alkoxy groups, or $R^3$ and $R^5$ and/or $R^4$ and $R^6$ taken together with the carbon atoms to which they are attached form a 5- or 6-membered ring which is optionally substituted with one to four substituents selected from $C_1$-$C_6$ alkyl groups, $C_3$-$C_6$ cycloalkyl groups, $C_1$-$C_6$ alkoxy groups, hydroxy or halogen,
X is a hydrocarbon group containing 1 to 20 carbon atoms and optionally 1 to 10 hetero atoms and comprising at least one group which is positively or negatively charged and
Y is a counterion.

As used herein, the term "electron-withdrawing group" refers to groups containing a multiple bond, such as a cyano or nitrilo group (—CN group), which is preferred, or a —COOR$^8$, —COR$^8$ or —CONR$^8{}_2$ group, wherein each R$^8$ is independently hydrogen, $C_1$-$C_{21}$ alkyl (preferably $C_1$-$C_6$ alkyl), $C_2$-$C_{21}$ alkenyl (preferably $C_2$-$C_6$ alkenyl), $C_2$-$C_{21}$ alkynyl (preferably $C_2$-$C_6$ alkynyl), $C_3$-$C_{21}$ cycloalkyl (preferably $C_3$-$C_8$ cycloalkyl) or $C_6$-$C_{10}$ aryl (preferably phenyl), each of those groups or preferred groups being unsubstituted or optionally substituted by one to three substituents selected from $C_1$-$C_6$ alkyl groups, halogen, hydroxy and $C_1$-$C_6$ alkoxy groups. Preferably at least one of residue $R^1$ and residue $R^2$ is a cyano group, most preferably both residue $R^1$ and residue $R^2$ each are a cyano group (CN group). It is also preferred that one residue is a cyano group and the other residue is a —COOR$^8$ group.

$R^3$, $R^4$, $R^5$ and $R^6$ are independently selected from hydrogen atoms, $C_1$-$C_{10}$ alkyl groups, $C_2$-$C_{10}$ alkenyl groups, $C_2$-$C_{10}$ alkinyl groups, $C_3$-$C_{10}$ cycloalkyl groups and $C_6$-$C_{10}$ aryl groups. Each of these groups can be unsubstituted or substituted by one to three substituents selected from $C_1$-$C_6$ alkyl groups, halogen, hydroxy and $C_1$-$C_6$ alkoxy groups. Alternatively, it is also possible that $R^3$ and $R^5$ and/or $R^4$ and $R^6$ taken together with the carbon atoms to which they are attached form a 5- or 6-membered ring which is optionally substituted with one to four substituents selected from $C_1$-$C_6$ alkyl groups, $C_3$-$C_6$ cycloalkyl groups, $C_1$-$C_6$ alkoxy groups, hydroxy or halogen. Preferably $R^3$, $R^4$, $R^5$ and $R^6$ are independently selected from hydrogen atoms, $C_1$-$C_6$ alkyl groups, $C_2$-$C_6$ alkenyl groups, $C_5$-$C_8$ cycloalkyl groups and a phenyl group, each of which is optionally substituted by one to three substituents, more preferably by one substituent as defined above. It is also preferred that $R^3$, $R^4$, $R^5$ and $R^6$ are independently selected from hydrogen atoms and unsubstituted $C_1$-$C_6$ alkyl groups, $C_2$-$C_6$ alkenyl groups, $C_5$-$C_8$ cycloalkyl groups and phenyl groups. If $R^3$ and $R^5$ and/or $R^4$ and $R^6$ are taken together with the carbon atom to which they are attached form a 5- or 6-membered ring, a 6-membered ring is preferred, and the rings are preferably unsubstituted or substituted with one substituent as defined above.

Most preferably at least one of $R^3$, $R^4$, $R^5$ and $R^6$, more preferably two of $R^3$, $R^4$, $R^5$ and $R^6$, are hydrogen atoms and the other groups $R^3$, $R^4$, $R^5$ and $R^6$ are $C_1$-$C_6$ alkyl groups or $C_2$-$C_6$ alkenyl groups. Most preferably $R^3$ and $R^4$ are hydrogen atoms and $R^5$ and $R^6$ are $C_1$-$C_6$ alkyl groups or $C_2$-$C_6$ alkenyl groups, more preferably $C_1$-$C_3$ alkyl groups.

The alkyl groups can be branched or straight chain. Preferred examples of $C_1$-$C_{10}$ alkyl groups are methyl, ethyl, propyl, isopropyl, butyl, sec-butyl, isobutyl, pentyl, neopentyl, hexyl, 2-ethylhexyl and octyl groups.

Preferred examples of $C_3$-$C_{10}$ cycloalkyl groups are cyclopropyl, cyclobutyl, cyclopentyl, cyclohexyl, cycloheptyl and cyclooctyl groups.

Preferred examples of $C_2$-$C_6$ alkenyl groups are ethenyl and n-propenyl groups.

Preferred examples of $C_6$-$C_{10}$ aryl groups are phenyl and naphthyl groups.

X is a linear, branched, cyclic or aromatic hydrocarbon group containing 1 to 20 carbon atoms, preferably 1 to 10 carbon atoms, more preferably 1 to 6 carbon atoms and optionally 1 to 10 hetero atoms, preferably 1 to 6 hetero atoms. According to the present specification, a hydrocarbon group containing hetero atoms can also contain functional groups such as hydroxyl groups. The hetero atoms are preferably selected from O, N, S and P atoms. It is important for the invention that residue X comprises at least one group, preferably one, two or three groups, which is positively or negatively charged. Preferably X is an alkyl, aryl, alkylaryl or alkylcycloalkyl group containing 1 to 20 carbon atoms and optionally 1 to 10 hetero atoms and comprising at least one group which is positively or negatively charged. The term "alkylaryl" or "alkylcycloalkyl" refers to an aryl or a cycloalkyl group which contains one or more alkyl substituents. Since the group X comprises at least one group which is positively or negatively charged, it will usually contain at least one hetero atom which bears the positive or the negative charge. Preferably residue X contains 1 to 6 hetero atoms, and the hetero atoms are preferably selected from nitrogen, oxygen, sulfur and phosphor atoms. If residue X is positively charged, it contains preferably at least one nitrogen atom which is positively charged, and thus the group which bears the positive charge is a quaternary ammonium group. Such compounds comprising a quaternary ammonium ion are particularly preferred for hair applications. If residue X contains a negatively charged group, the group which bears the negative charge is preferably an acid residue such as a residue of phosphoric acid or sulfuric acid or carboxylic acid.

It is also possible that residue X contains 1 to 4 unsaturated carbon-carbon bonds, preferably double bonds. Each carbon atom in residue X can optionally be substituted by a functional group, in particular by a hydroxyl or an amino group, preferably by a hydroxyl group. Preferably not more than three, more preferably not more than two carbon atoms of the residue X are substituted as defined above. Of course, if a carbon atom in residue X is substituted by an amino group, there can also be an unsaturated bond, preferably a double bond between the carbon atom and the nitrogen atom. It is also possible that residue X and residue Y together form a zwitter ion structure.

If the group which is positively or negatively charged in residue X is negatively charged, residue X carries preferably a single negative charge and is most preferably an acid residue such as a group —O—$SO_3^-$, —$COO^-$, —O—$PO_3H^-$, —O—$PO_3^{2-}$, —$SO_3^-$, —$PO_3H^-$ or $PO_3^{2-}$. Most preferred is group —O—$SO_3^-$, —$SO_3^-$ and a group —O—$PO_3H^-$. Typical examples of residue X which comprise at least one group which is negatively charged are alkylene groups which are optionally substituted by a cycloalkyl group or an aryl group or which is interrupted by a cycloalkyl group or an aryl group and which contains an acid residue as defined above. In a preferred embodiment the alkylene group is interrupted by one to three hetero atoms, preferably selected from oxygen and nitrogen atoms. The alkylene group contains preferably 1 to 10 carbon atoms, more preferably 1 to 6 carbon atoms. If the alkylene group is interrupted by a nitrogen atom, the nitrogen atom bears a further group $R^8$ as defined above.

A preferred example of a residue X having a single negative charge is a residue

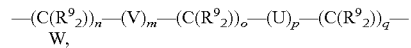

wherein each $R^9$ is independently hydroxy or defined as residue $R^8$ above and preferably is a hydrogen atom, hydroxy or a $C_1$-$C_3$ alkyl group, V and U are independently of each other a hetero atom, preferably an oxygen atom or a nitrogen atom (which carries a further group $R^8$ as defined above), more preferably an oxygen atom, n is an integer of 0 to 6 (preferably 1 to 6), m is 0 or 1, o is an integer of 0 to 6 (preferably 1 to 6), p is 0 or 1, q is an integer of 0 to 6 (preferably 1 to 6) and W is the residue bearing a negative charge, preferably an acid residue as defined above, most preferably a residue —O—$PO_3H^-$, a residue —$SO_3^-$ or a residue —O—$SO_3^-$, with the proviso that the total number of carbon atoms is 20 or less, preferably 10 or less, most preferably 1 to 6 and with the proviso that the total number of hetero atoms in residue X is 1 to 10, including the hetero atoms of functional group W, and with the proviso that index o is not 0, if index m and index p are both 1. Preferably not more than four residues $R^9$, more preferably not more than two residues $R^9$ are different from hydrogen, most preferably all residues $R^9$ are hydrogen.

Another preferred example of a residue X having a single negative charge is a residue —Ar—W, wherein Ar is an aromatic group, preferably a $C_6$-$C_{10}$ aromatic group, e.g. a phenylene or naphthylene group or a heterocyclic group, preferably a ring with 4 to 10 members, of which one or more, preferably 1 or 2, members are hetero atoms, preferably N, O or S atoms. The heterocyclic group can be saturated or unsaturated and hetero aromatic groups such as a pyridnylene group are also encompassed. W is as defined above.

It is also preferred that the at least one group which is positively or negatively charged in residue X is a group which has one positive charge. Most preferably this group which has one positive charge is a quaternary ammonium ion. In this case, residue X is preferably a residue of the formula

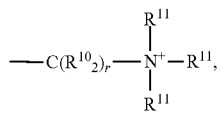

wherein each $R^{10}$ is independently hydrogen or $R^{11}$ and each $R^{11}$ is independently defined as residue $R^8$ above, preferably is hydrogen, a $C_1$-$C_{10}$, preferably $C_1$-$C_6$ alkyl group which may be interrupted by 1 to 4 hetero atoms, preferably by 1 or 2 hetero atoms, preferably by oxygen atoms and which may be substituted by 1 to 3 substituents selected from hydroxy groups, amino groups and $C_1$-$C_6$ alkyl, preferably $C_1$-$C_3$ alkyl groups, and index r is an integer from 1 to 10, preferably from 1 to 6, with the proviso that the total number of carbon atoms in residue X is 20 or less, preferably 1 to 10, and that the total number of hetero atoms including the nitrogen atom and all hetero atoms of functional groups is 1 to 10, preferably 1 to 6, more preferably 1 to 4. Compounds comprising at least one quaternary ammonium ion as defined above are particularly useful for hair applications such as hair care products, shampoo, hair sprays, etc. In one embodiment of the invention, residue $R^{11}$ may contain a negative charge and therefore encompass residue Y, e.g. one residue $R^{11}$ can be an alkyl group which is substituted with a functional group bearing a negative charge such as an —$SO_3^-$ group or a similar group.

In a preferred embodiment, residue XY is a zwitter ion having a positive charge and a negative charge, the number of carbon atoms, heteroatoms and functional groups being as defined above.

The exact structure of residue X is not relevant, as long as it contains at least one positive or negative charge which makes the molecule water-soluble and/or which provides good adhesiveness to hair. Preferably, X contains one, two or three positive or negative charges.

Residue Y is a counterion which should balance the charge of residue X. The exact chemical nature of the counterion Y is not important for the invention, as long as counterion Y does not negatively interfere with the advantageous properties of the UV-A absorbent and in particular as long as Y is dermatologically and cosmetically acceptable. If residue X is negatively charged, residue Y is preferably a quaternary ammonium ion, an alkali metal or an earth alkali metal ion, more preferably a sodium, potassium, calcium or magnesium ion, but it is also possible that residue Y is a positively charged organic residue, e.g. an ammonium ion such as a triethanol ammonium ion, an aminomethyl propanol ion or a tromethamine ion. If residue Y has more positive charges than residue X has negative charges, residue Y contains a further counterion which balances the additional charge or more than one residue X is balanced by one residue Y. For example, residue Y can be

(or $M^{s+}(A^-)_{s-1}$, wherein $M^{s+}$ is an ion with s positive charges and $A^-$ is an ion with a single negative charge, e.g. a halogen atom, and s is 1 to 3, preferably 1 or 2, more preferably 1.

If residue X is positively charged, residue Y is negatively charged and preferably residue Y is a halogen atom, such as a chlorine, bromine or iodine atom. If residue Y has more negative charges than residue X has positive charges, residue Y contains a further counterion which balances the additional charge or more than one residue X is balanced by one residue Y. For example, residue Y can be

or $M^{s-}(A^+)_{s-1}$, wherein $M^{s-}$ is an ion with s negative charges and $A^+$ is an ion with one positive charge, e.g. an alkali metal ion, and s is 1 to 3, preferably 1 or 2, more preferably 1.

If residue X carries more than one charge, more than one counterion Y can be present or residue Y carries more than one countercharge. It is important that residue Y is selected so that the total molecule of the formula I is not charged.

It is also possible that X and Y are chemically bonded together, such as in moieties as —$(CH_2)_r N^+(R^{11})_2$—$(CH_2)_t$—$SO_3^-$, with r is as defined above and t is an integer of 1 to 10, preferably 1 to 5, e.g. 2. In such embodiments, residues X and Y together form a zwitter ion structure.

Preferably residues $R^1$ to $R^6$, X and Y are selected so that the molecule has a water-solubility of at least 10 g/l, preferably at least 50 g/l, more preferably at least 100 g/l. If the water-solubility of a compound of formula I is not sufficiently high, the substitution pattern can be changed, e.g. the number of carbon atoms in residues $R^3$ to $R^6$ can be reduced, aryl or cycloalkyl residues which can reduce the water-solubility can be removed from some or all of the residues, and hydrophilic substituents such as hydroxy groups can be included.

Compounds which have a particularly high adherence to hair, such as the quaternary ammonium ions of the formula —$C(R^{10}_2)_r$—$N^+(R^{11})_3$ as defined above, may have a lower water-solubility.

Preferred compounds of the present invention are

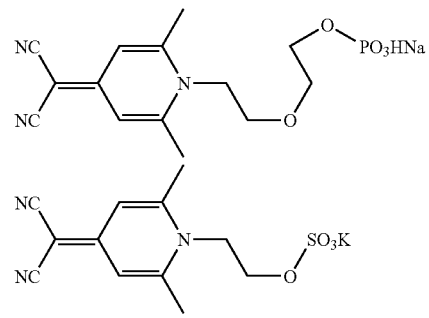

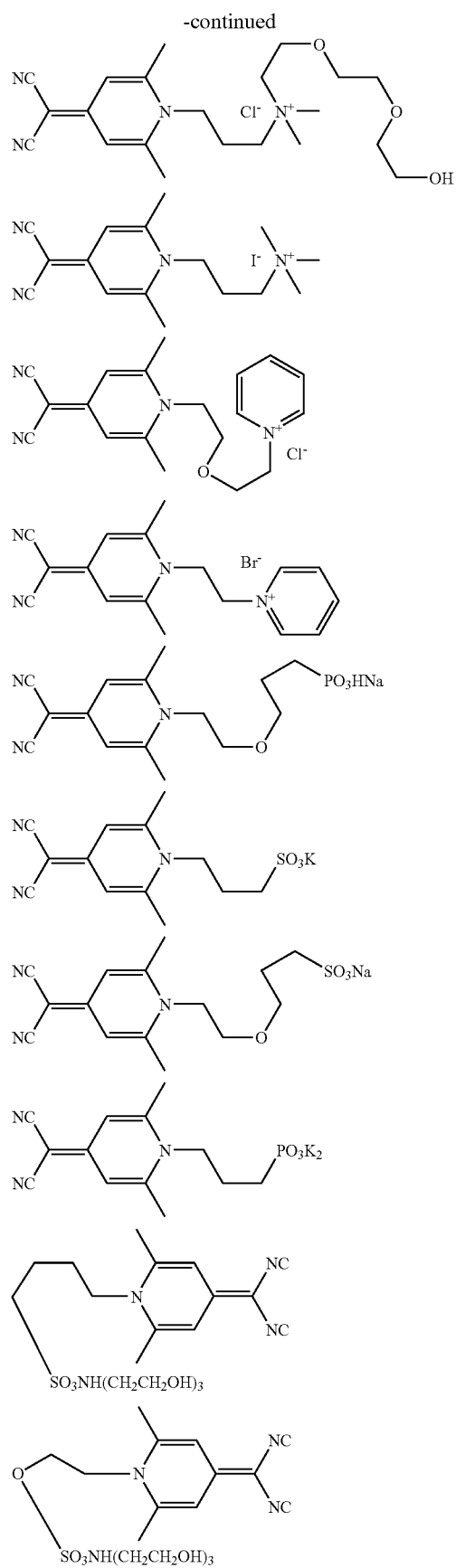
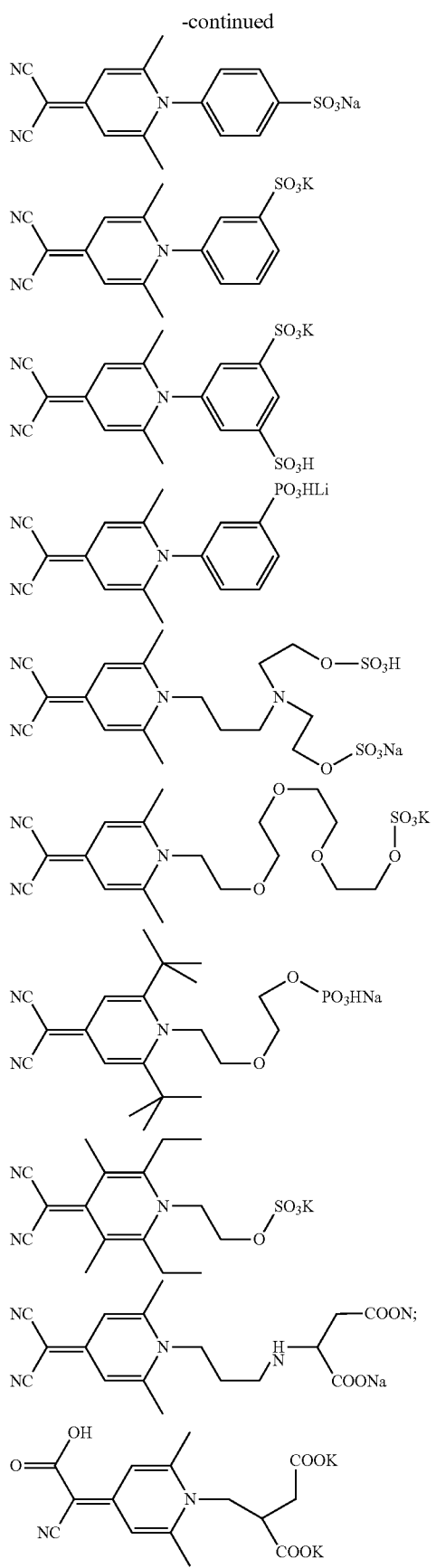

-continued
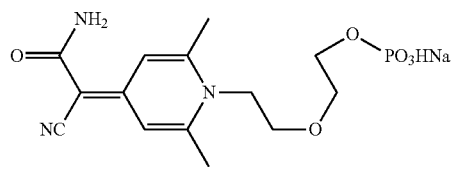
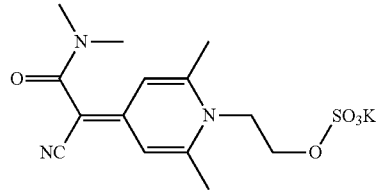
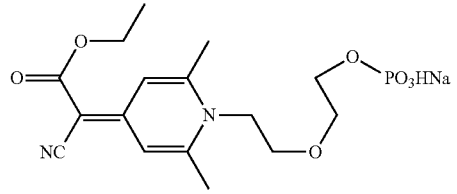
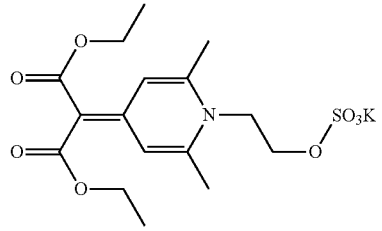
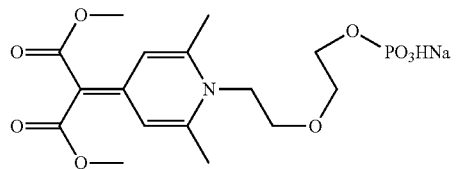
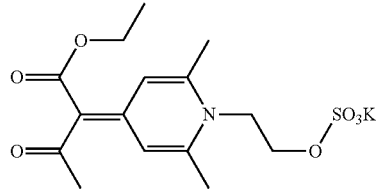
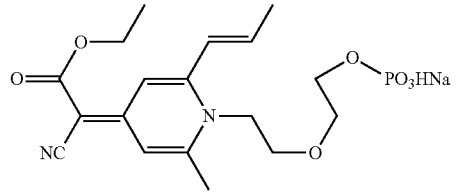
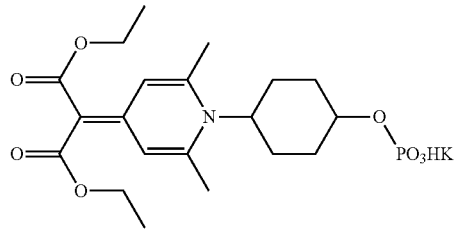
-continued
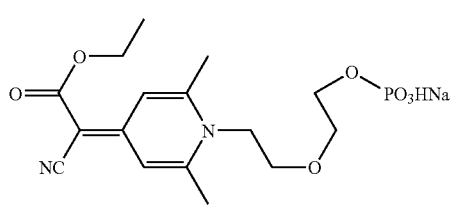
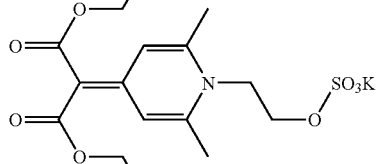
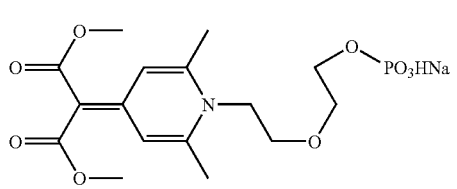
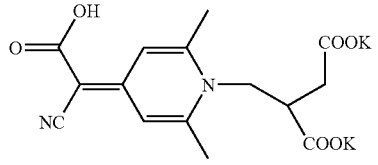
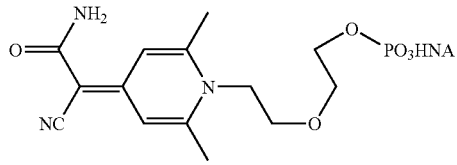
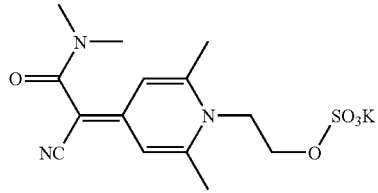
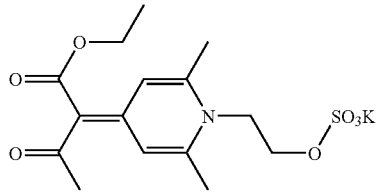
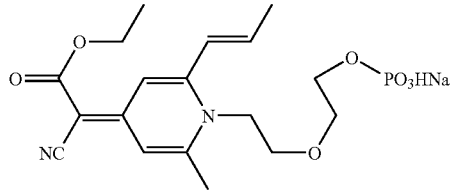

-continued

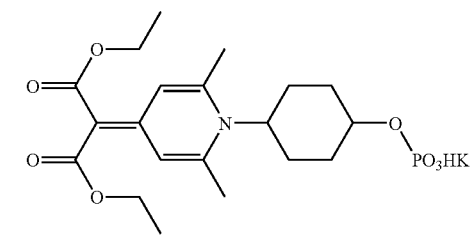

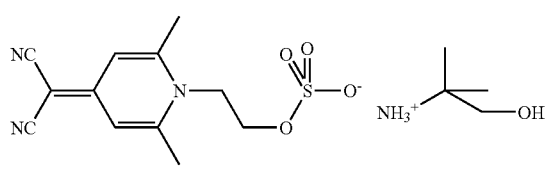

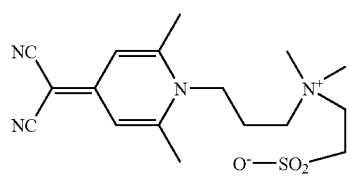

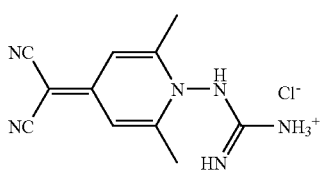

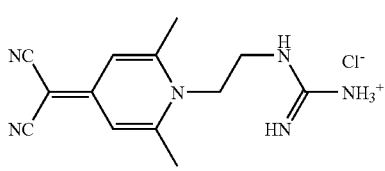

and combinations or interchangements of the varied structure elements.

The compounds

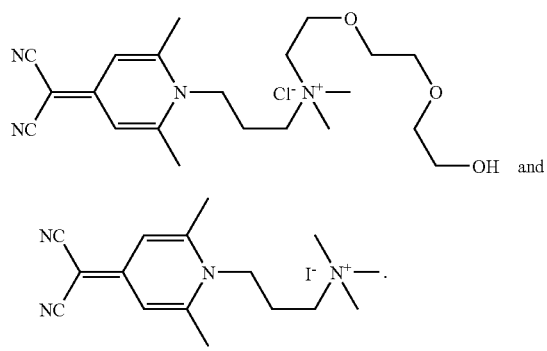

may not have a high water-solubility, but they are particularly preferred for hair care applications.

The compounds of formula (I) can be prepared by methods known per se. Some methods are disclosed in the examples, and a skilled person can easily adapt these methods to prepare other compounds of formula (I).

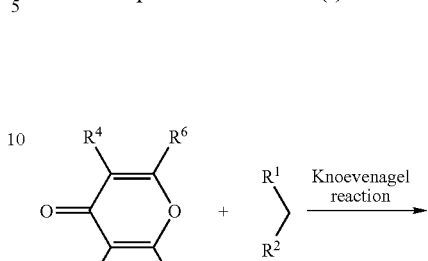

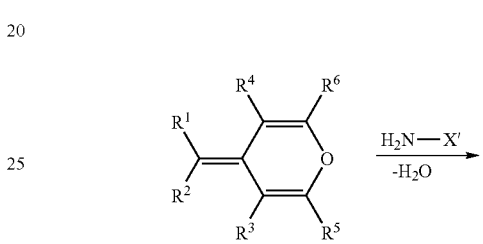

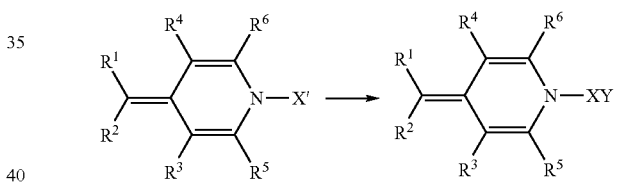

where X' is a precursor structure of XY.

Phosphate residues of the type —O—$PO_3^{2-}$ can for example be prepared from the corresponding alcohol function using e.g. $POCl_3$ with a base as e.g. triethylamine [see e.g. M.-Z. Liu et al., Carbohydr. Res. 330 (3), 413-420 (2001)], with $P_2O_5$ and $H_3PO_4$ [see e.g. K. Buss et al., J. Med. Chem. 44 (19), 3166-3174 (2001)] or by enzymatic methods.

Sulfate residues of the type —O—$SO_3^-$ can for example be prepared from the corresponding alcohol function using e.g. $SO_3$× pyridine [see e.g. W. J. Sanders et al., Tetrahedron 53 (48), 16391-16422 (1997)], $SO_3$× $NEt_3$ [see e.g. B. Ferla et al., Tetrahedron 55 (32), 9867-9880 (1999)], chlorosulfonic acid [see e.g. G. Dekany et al., J. Carbohydr. Chem. 16 (1), 11-24 (1997)] or $H_2SO_4$ [see e.g. S. P. Gaur et al., Indian J. Chem. Sect B 21 (1), 46-51 (1982)].

Some further preferred compounds of the invention and general methods for their production are shown below:

Process a)
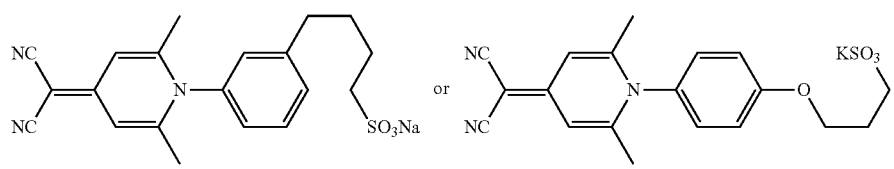
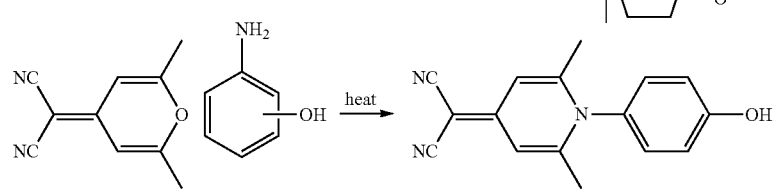
Process b)
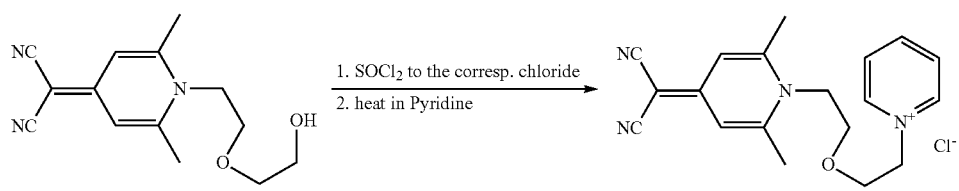
analogously to:
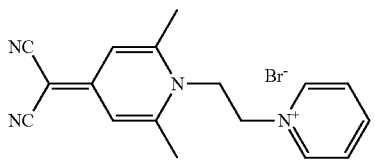
Process c)
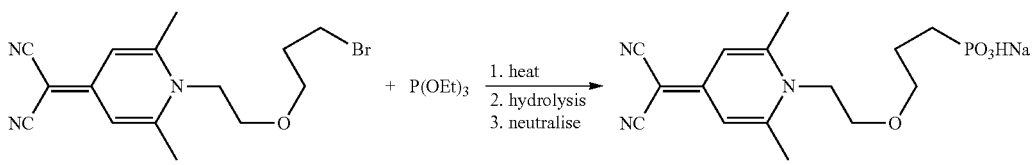
Analogously for
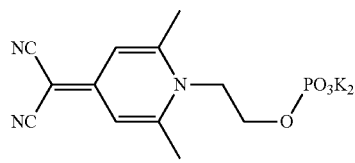
Process d)
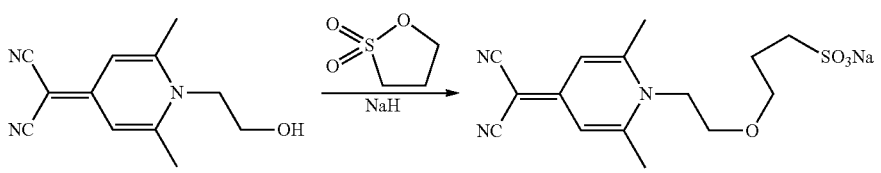
Analogously for:
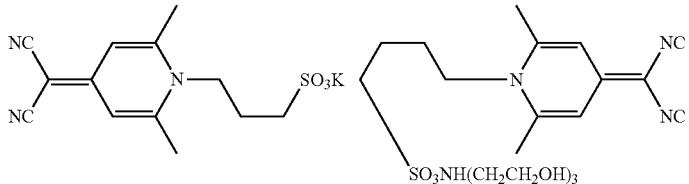

-continued
Process e)
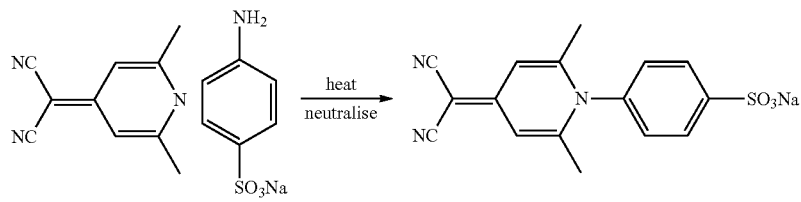
ditto for
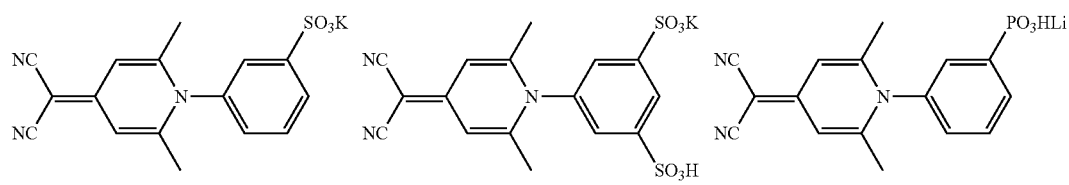
Process f)
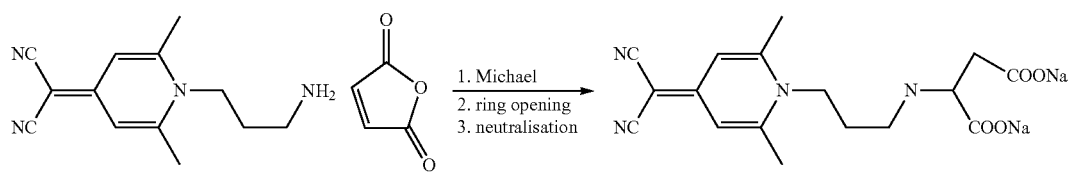
Process g)
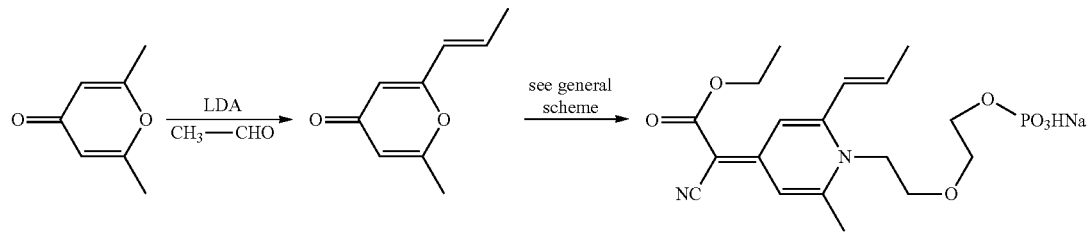
Process h)
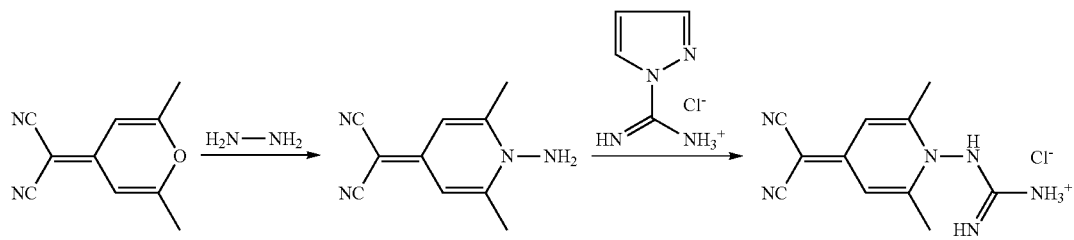
Process i)
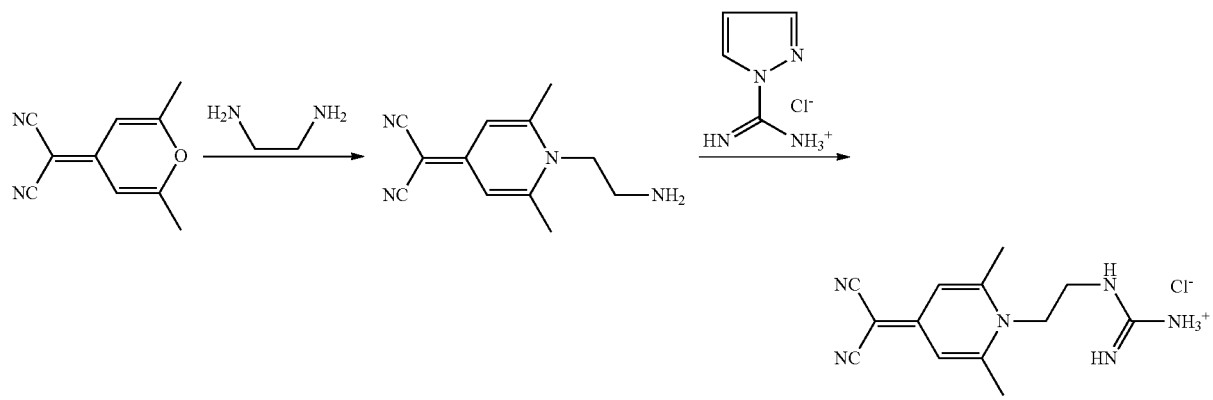

-continued

Process j)

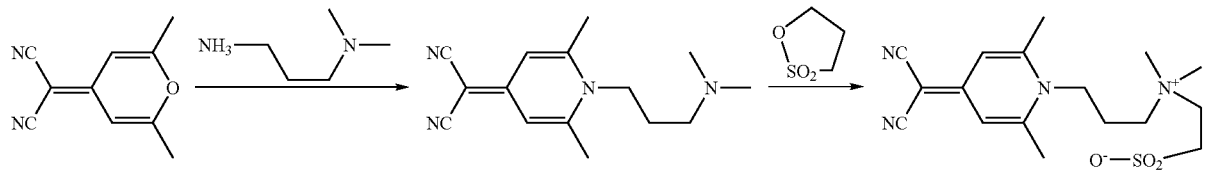

Similar to example 2:

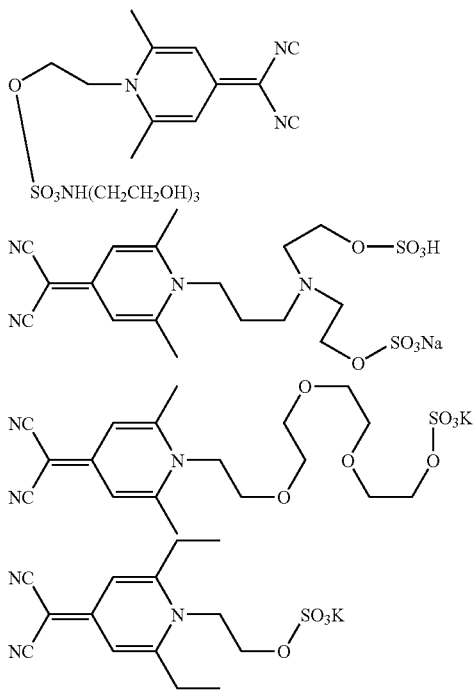

Similar to example 1:

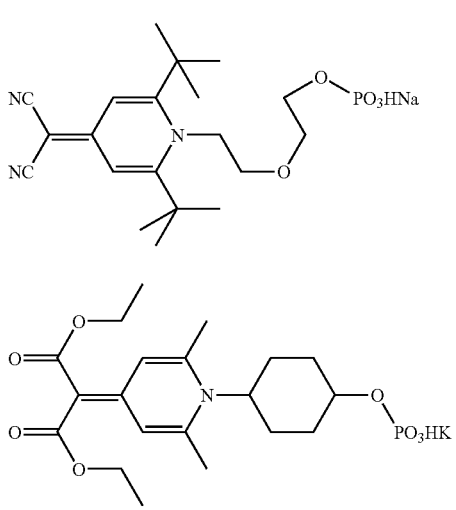

The following compounds of formula (I) are particularly preferred:

Residues $R^1$ and $R^2$ are both cyano groups, residues $R^3$, $R^4$, $R^5$ and $R^6$ are independently selected from hydrogen atoms and $C_1$-$C_6$ alkyl groups, Y is a counterion which balances the charge of residue X, preferably an alkali metal ion or a halogen ion, depending on the charge of X, and a) X is a residue

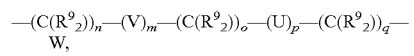

wherein each $R^9$ is independently hydrogen, hydroxy or $C_1$-$C_3$ alkyl, V and U are an oxygen atom, n is an integer of 1 to 3, m is 0 or 1, p is 0 or 1, wherein at least one of m and p is 1, o is an integer of 1 to 3, and q is an integer of 1 to 3, and W is a residue —O—$PO_3H^-$ or a residue —O—$SO_3^-$, or b) X is a residue

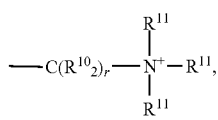

wherein residues $R^{10}$ are independently selected from hydrogen atoms, hydroxyl groups and $C_1$-$C_3$ alkyl groups, and residues $R^{11}$ are independently selected from hydrogen atoms and $C_1$-$C_6$ alkyl groups which are optionally interrupted by 1 to 2 hetero atoms and which are optionally substituted by 1 to 3 hydroxyl groups, and r is an integer of 1 to 6, or c) X is a residue

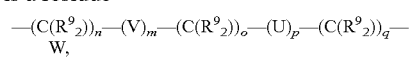

wherein each $R^9$ is independently hydrogen or methyl, V and U are an oxygen atom, n is an integer of 1 to 3, m is 0 or 1, p is 0 or 1, wherein at least one of m and p is 1, o is an integer of 1 to 3, and q is an integer of 1 to 3, and W is a residue —O—$PO_3H^-$ or a residue —O—$SO_3^-$, or d) X is a residue

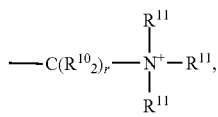

wherein residues $R^{10}$ are independently selected from hydrogen atoms, hydroxyl groups and $C_1$-$C_3$ alkyl groups, and residues $R^{11}$ are independently selected from hydrogen atoms and $C_1$-$C_6$ alkyl groups which are optionally interrupted by 1 to 2 oxygen atoms and which are optionally substituted by 1 to 3 hydroxyl groups, and r is an integer of 1 to 3, or e) X is a residue

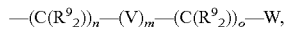

wherein each $R^9$ is independently hydrogen or methyl, V is an oxygen atom, n is an integer of 1 to 3, m is 1, o is an integer of 1 to 3, and W is a residue —O—$PO_3H^-$ or a residue —O—$SO_3^-$, or f) X is a residue

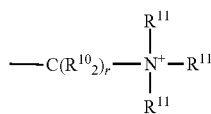

wherein residues $R^{10}$ are independently selected from hydrogen atoms and $C_1$-$C_3$ alkyl groups, and residues $R^{11}$ are independently selected from $C_1$-$C_6$ alkyl groups which are optionally interrupted by 1 to 2 hetero atoms and which are optionally substituted by 1 to 3 hydroxyl groups, and r is an integer of 1 to 3, or g) X is a residue

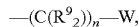

wherein each $R^9$ is independently hydrogen, hydroxy or $C_1$-$C_3$ alkyl, and n is an integer of 1 to 6, and W is a residue —O—$PO_3H^-$ or a residue —O—$SO_3^-$, or h) X is a residue

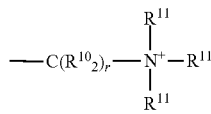

wherein residues $R^{10}$ are independently selected from hydrogen atoms, hydroxyl groups and $C_1$-$C_3$ alkyl groups, and two residues $R^{11}$ are $C_1$-$C_3$ alkyl groups, and one residue $R^{11}$ is a $C_1$-$C_6$ alkyl group which is interrupted by 1 or 2 oxygen atoms and which is optionally substituted by 1 to 3 hydroxyl groups, and r is an integer of 1 to 3 or the residues $R^{11}$ form together with the nitrogen atom a pyridinyl group which is unsubstituted or substituted with 1 to 5, preferably 1 to 3 substituent groups $R^8$ as defined above.

i) One of the residues as defined in items a) to h) above, wherein one residue $R^9$ or $R^{10}$ is a saturated or unsaturated nitrogen containing hydrocarbon group containing up to 5 carbon atoms and one or two nitrogen atoms.

Those compounds of the present invention which comprise a residue

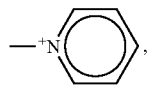

which is unsubstituted or substituted with 1 to 5, preferably 1 to 3 substituent groups $R^8$ as defined above, have a particularly high water-solubility and those compounds of formula (I) are especially preferred.

The present invention also relates to compositions comprising a compound of formula (I) formulated into a suitable support or substrate. Typically the compositions of the invention are adopted for protecting a material that is sensitive to ultraviolet radiation, in particular solar radiation, and comprises an effective photoprotective amount of at least one of the compounds of formula (I). In one preferred embodiment of the invention such compositions are suited for protecting the skin and/or hair against the deleterious effect of UV radiation. In this case the compositions according to the invention are cosmetic or pharmaceutical compositions which comprise a topically applicable, cosmetically or pharmaceutically acceptable vehicle and diluent as carrier. According to another embodiment of the invention the compounds of formula (I) can be incorporated into a plastic substrate. The compounds of formula (I) may also be used to stabilize photosensitive ingredients in topical formulations particularly colorants, such as FD&C and D&C colorants, curcumin, riboflavin, lactoflavine, tartrazine, chinolinyellow, cochenille, azorubin, amaranth, ponceau 4R, erythrosin, indigotin, chlorophylle, chlorophyllin, caramel, Carbo medicinalis, carotinoids, bixin, norbixin, annato, orlean, capsanthin, capsorubin, lycopin, xanthophylle, flavoxanthin, lutein, kryptoaxanthin, rubixanthin, violaxanthin, rhodoxanthin, canthaxanthin, betanin, anthocyans, vitamins such as vitamin A, vitamin K1, vitamin C or other active ingredients.

The compounds of formula (I) have adsorption maxima in the UV-A region. For the preparation of light screening agents, especially of preparations for dermatological and/or cosmetic use, such as skin protection and sunscreen formulations for everyday cosmetics a compound of formula (I) may be incorporated in auxiliary agents, e.g. a cosmetic base, which are conventionally used for such formulations. Where convenient, other conventional UV-A and/or UV-B screening agents, preferably a pigment, may also be added. The combination of UV filters may show a synergistic effect. The preparation of said light screening agents is well known to the skilled artisan in this field. The concentration of UV filters is varied in a wide range. For example, the amount of compounds of formula I and optionally an additional hydrophilic and/or lipophilic UV-A or UV-B screening agent other than the compounds of formula (I) may be in the range of from 0.5 to 12% by weight of the total composition. These additional screening agents are advantageously selected from the compounds listed below without being limited thereto:

Examples of UV-B or broad spectrum screening agents, i.e. substances having absorption maximums between about 290 and 340 nm, which come into consideration for combination with the compounds of the present invention are for example the following organic and inorganic compounds:

Acrylates such as 2-ethylhexyl 2-cyano-3,3-diphenylacrylate (octocrylene, PARSOL® 340), ethyl 2-cyano-3,3-diphenylacrylate and the like;

Camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like;

Cinnamate derivatives such as octyl methoxycinnamate (PARSOL® MCX), ethoxyethyl methoxycinnamate, diethanolamine methoxycinnamate (PARSOL®

Hydro), isoamyl methoxycinnamate and the like as well as cinnamic acid derivatives bond to siloxanes;

p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate, Benzophenones such as benzophenone-3, benzophenone-4,2,2', 4,4'-tetrahydroxy-benzophenone, 2,2'-dihydroxy-4,4'-dimethoxybenzophenone and the like;

Esters of Benzalmalonic acid such as di-(2-ethylhexyl) 4-methoxybenzalmalonate;

Esters of 2-(4-ethoxy-anilinomethylene)propandioic acid such as 2-(4-ethoxy anilinomethylene)propandioic acid diethyl ester as described in the European Patent Publication EP 0895 776;

Organosiloxane compounds containing benzmalonate groups as described in the European Patent Publications EP 0358584 B1, EP 0538431 B1 and EP 0709080 A1;

Drometrizole trisiloxane (Mexoryl XL);

Pigments such as microparticulated $TiO_2$, and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.

Imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like.

Salicylate derivatives such as isopropylbenzyl salicylate, benzyl salicylate, butyl salicylate, octyl salicylate (NEO HELIOPAN OS), isooctyl salicylate or homomethyl salicylate (homosalate, HELIOPAN) and the like.

Triazine derivatives such as octyl triazone (UVINUL T-150), dioctyl butamido triazone (UVASORB HEB), bis ethoxyphenol methoxyphenyl triazine (Tinosorb S) and the like.

Examples of broad spectrum or UV A screening agents i.e. substances having absorption maximums between about 320 and 400 nm, which come into consideration for combination with the compounds of the present invention are for example the following organic and inorganic compounds:

Dibenzoylmethane derivatives such as 4-tert. butyl-4'-methoxydibenzoyl-methane (PARSOL® 1789), dimethoxydibenzoylmethane, isopropyldibenzoylmethane and the like;

Benzotriazole derivatives such as 2,2'-methylene-bis-(6-(2H-benzotriazole-2-yl)-4-(1,1,3,3,-tetramethylbutyl)-phenol (TINOSORB M) and the like;

phenylene-1,4-bis-benzimidazolsulfonic acids or salts such as 2,2-(1,4-phenylene)bis-(1H-benzimidazol-4,6-disulfonic acid) (Neoheliopan AP);

amino substituted hydroxybenzophenones such as 2-(4-Diethylamino-2-hydroxy-benzoyl)-benzoic acid hexylester as described in the European Patent Publication EP 1046391;

Pigments such as microparticulated ZnO or $TiO_2$ and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g., 3,3-Diphenylacrylate derivatives as described in the European Patent Publications EP 0 514 491 B1 and EP 0 780 119 A1;

Benzylidene camphor derivatives as described in the U.S. Pat. No. 5,605,680;

Organosiloxanes containing benzmalonate groups as described in the European Patent Publications EP 0358584 B1, EP 0538431 B1 and EP 0709080 A1.

The compositions of the invention can also contain usual cosmetic adjuvants and additives, such as preservatives/antioxidants, fatty substances/oils, water, organic solvents, silicones, thickeners, softeners, emulsifiers, additional sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, in particular those suited for providing an additional photoprotective effect by physically blocking out ultraviolet radiation, or any other ingredients usually formulated into cosmetics, in particular for the production of sunscreen/antisun compositions. The necessary amounts of the cosmetic and dermatological adjuvants and additives can, based on the desired product, easily be chosen by a skilled artisan in this field and will be illustrated in the examples, without being limited hereto.

An additional amount of antioxidants/preservatives is generally preferred. Based on the invention all known antioxidants usually formulated into cosmetics can be used. Especially preferred are antioxidants chosen from the group consisting of amino acids (e.g. glycine, histidine, tyrosine, tryptophane) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, y-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinsulfoximine, buthioninsulfone, penta-, hexa-, heptathioninsulfoximine) in very low compatible doses (e.g. pmol bis µmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbylacetate), tocopherol and derivates (such as vitamin-E-acetate), mixtures of nat. vitamin E, vitamin A and derivatives (vitamin-A-palmitate and -acetate) as well as coniferylbenzoat, rutinic acid and derivatives, α-glycosylrutin, ferulic acid, furfurylidenglucitol, carnosin, butylhydroxytoluene, butylhydroxyanisole, trihydroxybutyrophenone, urea and its derivatives, mannose and derivatives, zinc and derivatives (e.g. ZnO, ZnSO$_4$), Selen and derivatives (e.g. selenomethionine), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount about 0.01 wt. % to about 10 wt. % of the total weight of the composition of the present invention. Preferably, one or more preservatives/antioxidants are present in an amount about 0.1 wt. % to about 1 wt. %.

Typically formulations also contain surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/C$_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP Eicosene copolymer, acrylates/C$_{10-30}$-alkyl acrylate crosspolymer, PEG-20 sorbitan isostearate, sorbitan isostearate, and mixtures thereof. The one or more emulsifiers are present in a total amount about 0.01 wt. % to about 20 wt. % of the total weight of the composition of the present invention. Preferably, about 0.1 wt. % to about 10 wt. % of emulsifiers are used.

The lipid phase can advantageously be chosen from:

mineral oils and mineral waxes;

oils such as triglycerides of caprinic acid or caprylic acid, preferable castor oil;

oils or waxes and other natural or synthetic oils, in an preferred embodiment esters of fatty acids with alcohols e.g. isopropanol, propyleneglycol, glycerine or esters of fatty alcohols with carbonic acids or fatty acids;

alkylbenzoates; and/or silicone oils such as dimethylpolysiloxane, diethylpolysiloxane, diphenylpolysiloxane, cyclomethicones and mixtures thereof.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaureate, n-decyloleat, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the formulation of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyidimethicone, hexamethylcyclotrisiloxane, polydimethylsiloxane, poly(methylphenylsiloxane) and mixtures thereof.

Other fatty components which can advantageously be incorporated in formulations of the present invention are isoeikosane; neopentylglykoldiheptanoate; propyleneglycol-dicaprylate/dicaprate; caprylic/capric/diglyceryisuccinate; butyleneglycol caprylat/caprat; C$_{12-13}$-alkyllactate; di-C$_{12-13}$ alkyltartrate; triisostearin; dipentaerythrityl hexacaprylat/hexacaprate; propyleneglycolmonoisostearate; tricaprylin; dimethylisosorbid. Especially beneficial is the use of mixtures C$_{12-15}$-alkylbenzoate and 2-ethylhexylisostearate, mixtures C$_{12-15}$-alkylbenzoate and isotridecylisononanoate as well as mixtures of C$_{12-15}$-alkylbenzoate, 2-ethylhexylisostearate and isotridecylisononanoate.

The oily phase of the formulation of the present invention can also contain natural vegetable or animal waxes such as bee wax, china wax, bumblebee wax and other waxes of insects as well as shea butter and cocoa butter.

A moisturizing agent may be incorporated into a composition of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimethicone, cyclomethicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (EN-JAY), diisopropyl adipate, hydroxybenzoate esters, benzoic acid esters of C$_{9-15}$-alcohols, isononyl iso-nonanoate, ethers such as polyoxypropylene butyl ethers and polyoxypropylene cetyl ethers, and C$_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt. % to about 20 wt. % of the total weight of the composition. The preferred amount of emollient is about 2 wt. % to about 15 wt. %, and most preferably about 4 wt. % to about 10 wt. %.

Moisturizers that bind water, thereby retaining it on the skin surface are called humectants. Suitable humectants can be incorporated into a composition of the present invention such as glycerin, polypropylene glycol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a composition of the present invention, preferably about 1 wt. % to about 5 wt. %.

The aqueous phase of the compositions of the present invention can contain the usual cosmetic additives such as alcohols, especially lower alcohols, preferably ethanol and/or isopropanol, low diols or polyols and their ethers, preferably propyleneglycol, glycerine, ethyleneglycol, ethyleneglycol monomethyl- or monobutylether, propyleneglycol monomethyl- or -monoethyl- or -monobutylether, diethyleneglycol monomethyl- or monoethylether and analogue products, polymers, foam stabilizers; electrolytes and especially one or more thickeners. Thickeners that may be used in formulations of the present invention to assist in making the consistency of a product suitable include carbomer, siliciumdioxide, magnesium and/or aluminum silicates, beeswax, stearic acid, stearyl alcohol polysaccharides and their derivatives such as xanthan gum, hydroxypropyl cellulose, polyacrylamides, acrylate crosspolymers preferably a carbomer, such as Carbopole® of type 980, 981, 1382, 2984, 5984 alone or mixtures thereof. Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the composition of the present invention, preferably, 1 wt. % to about 5 wt. %.

The addition of electrolytes into the composition of the present invention may be necessary to change the behavior of a hydrophobic emulsifier. Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the composition of the present invention.

The cosmetic compositions of the invention are useful as compositions for photoprotecting the human epidermis or hair against the damaging effect of ultraviolet irradiation, as sunscreen compositions. Such compositions can, in particular, be provided in the form of a lotion, a thickened lotion, a gel, a cream, a milk, an ointment, a powder or a solid tube stick and can be optionally be packaged as an aerosol and can be provided in the form of a mousse, foam or a spray. When the cosmetic composition according to the invention are provided for protecting the human epidermis against UV radiation or as sunscreen composition, they can be in the form of a suspension or dispersion in solvents or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

The compounds of the present invention protect the skin and hair against dangerous UV-A radiation. They can be complemented by other UV-A sunscreens in the organic phase thus giving rise to higher sun protection. The compounds can easily be incorporated into different cosmetic compositions, and they show protection against a longer wavelength than other known UV-A sunscreens and in particular than other commercial, water-soluble UV-A sunscreens, thus being a real UV-A filter and not an UV-A/UV-B gap filter and shielding the skin up to the visible rays without being colored. Furthermore, it is a significant advantage of the novel compounds of formula (I) that they show higher extinctions than other known water-soluble UV-A sunscreens and in particular even a better extinction than the present commercial water-soluble UV-A sunscreens, thus giving better protection. The compounds of formula (I) additionally show an excellent photostability. Surprisingly the compounds of formula (I) also stabilize emulsions and can therefore serve as co-emulsifiers for the compositions of the present invention, if these are in the form of an emulsion. The compounds of formula (I) show a very low skin penetration and have excellent adhesiveness to skin and hair.

The following examples are provided to further illustrate the processes and compositions of the present invention. These examples are illustrative only and are not intended to limit the scope of the invention in any way.

EXAMPLE 1

4-dicyanomethylene-2,6-dimethyl-1,4-dihydropyridine-N-(ethyloxy-ethyloxyphosphate ester mono sodium salt)

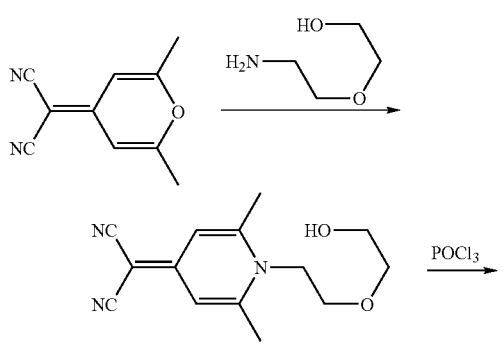

-continued

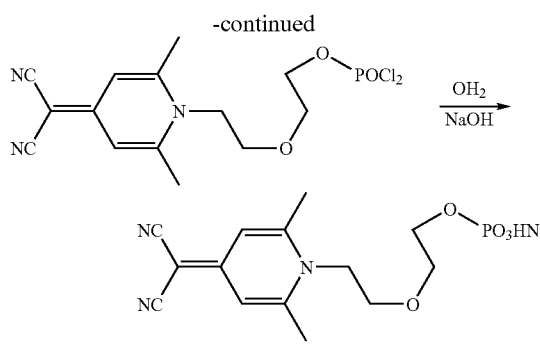

a) 4-dicyanomethylene-2,6-dimethyl-1,4-dihydropyridine-N-(ethyloxy-ethanol)

A 350 ml three necked reaction flask, equipped with a thermometer, a reflux condenser and an oil bath with a magnetic stirrer was charged with 30.1 g (175 mmol) of 4-Dicyanomethylene-4H-pyran (prepared according Helv. Chim. Acta 1962, 1908-1917) and 20.2 g (192 mmol) of 2-(2-Aminoethoxy)-ethanol (Fluka) in 150 ml of n-Butanol and heated for 90 Min. under Ar atmosphere. After cooling the bulky suspension was filtered the filter residue was washed consecutively with Ethylacetate, Diisopropylether and Pentane, to yield after drying 20.3 g of slightly fawn crystals. M.p. 157-158° C. UV(THF) 360 and 372 nm (32'332)

b) 4-dicyanomethylene-2,6-dimethyl-1,4-dihydropyridine-N-(ethyloxy-ethyloxyphosphate ester mono sodium salt)

A 750 ml four necked reaction flask, equipped with a thermometer, dropping funnel, a reflux condenser, pH electrode and a cooling bath with a magnetic stirrer was charged under Argon with 19.5 g (75 mmol) of the above prepared 4-Dicyanomethylene-2,6-dimethyl-1,4-dihydropyridine-N-(ethyloxy-ethanol) and 13.6 ml (97.5 mmol) of Triethylamine (Fluka) in 250 ml of THF and cooled to 10° C. Then a solution of 13.8 g (90 mmol) of $POCl_3$ in 50 ml of THF is added by means of the dropping funnel within 15 Min. This mixture is stirred for 16 hours at room temperature, the reaction is traced by HPLC and the precipitate is filtered off to remove the $NEt_3 \times HCl$ formed. The filtrate is again cooled to 10° C. and 1 mg of 18-crown-6 is added followed by 97.5 ml of 2.0-n aqueous NaOH while checking the pH. The reaction was stirred for further 90 Min. and additional 2.0-n aqueous NaOH was added at 20° C. until pH=4 was reached. At this point the aqueous phase was separated and washed with 100 ml of Ethylacetate. By addition of 50 ml of saturated aqueous NaCl solution the product precipitate and could be filtered off and washed with 200 ml of Acetone. After drying 18.2 g of colorless crystals were obtained.; Solubility 168 g/l in Water. This salt was recrystallized from DMF. M.p. 158-159° C.; UV (Water) 350 nm (E=979). The photostability of this product was measured according to Berset et al., *Internat. J. Cosmetic Science* 18: 167-177 (1996) using a solution of a mixture of water/glycerol=7:3 as liquid phase. The product was found to be photostable.

EXAMPLE 2

4-dicyanomethylene-2,6-dimethyl-1,4-dihydropyridine-N-(ethyloxysulfate ester mono sodium salt)

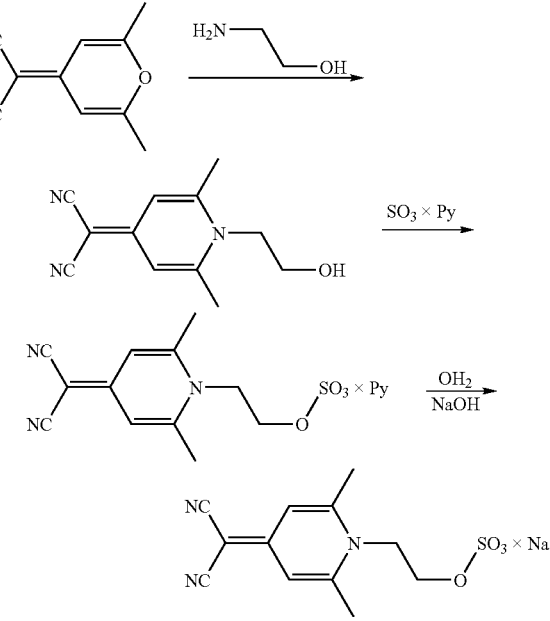

a) 4-dicyanomethylene-2,6-dimethyl-1,4-dihydropyridine-N-ethane-2-ol

A 350 ml three necked reaction flask, equipped with a thermometer, a reflux condenser and an oil bath with a magnetic stirrer was charged with 25.8 g (150 mmol) of 4-dicyanomethylene-4H-pyran (prepared according Helv. Chim. Acta 1962, 1908-1917) in 100 ml of ethanolamine (Fluka) and heated to 80° C. for 30 Min. under Ar atmosphere. Shortly after the start, an exothermic reaction is observed. After cooling, the mixture is diluted with 100 ml of n-Butanol and filtered off. The filter residue was washed consecutively with 2×10 ml of cold water, and 2×100 ml of Acetone. After drying 17.5 g of slightly yellowish crystals were obtained. M.p. 267-268° C. UV(THF) 360 and 372 nm (26'305).

b) 4-dicyanomethylene-2,6-dimethyl-1,4-dihydropyridine-N-(ethyloxysulfate ester mono sodium salt)

A 100 ml reaction flask equipped with a stirrer, reflux condenser, thermometer, oil bath and Ar atmosphere is charged with 2.15 g (10 mmol) of the above 4-dicyanomethylene-2,6-dimethyl-1,4-dihydropyridine-N-ethane-2-ol and 1.91 g (12 mmol) of sulfurtrioxyde-pyridine complex (Fluka) in a mixture of 30 ml of acetonitrile/pyridine=9:1. This mixture is heated with strong stirring to 60° C. for 30 Min. Already after 10 Min. practically no starting material could be detected by HPLC. At room temperature the mixture was diluted with 30 ml of acetone and filtered. The residue was washed with acetone, diisopropyl ether and pentane and dried to yield 3.1 g of colorless crystal m.p. 209-210° C. This material was dissolved in 30 ml of water. One equivalent of aq. 1-n NaOH was added and the mixture was stirred for 15 Min. and concentrated at the rotavap using high vacuum. 50 ml of water were added again to the residue and it was concentrated as above. This process was repeated again two times, until no smell of pyridine could be traced. The dry substance was again dissolved in five times its weight of water, precipitated by the addition of 200 ml of THF, filtered and the residue was washed with THF and acetone to yield 2.9 g of colorless crystals. M.p. 198° C. decomposition; UV(water) 352 nm (E=1261). Solubility>=25 g/l in Water. The photostability of this product was measured according to Berset et al., *Internat. J. Cosmetic Science* 18: 167-177 (1996) using a solution of a mixture of water/glycerol=7:3 as liquid phase. The product was found to be photostable.

EXAMPLE 3

4-dicyanomethylene-2,6-dimethyl-1,4-dihydropyridine-N-[3-(N,N-dimethyl-N-(ethoxy-ethoxy ethanol-yl)-propyl-ammonium iodide]

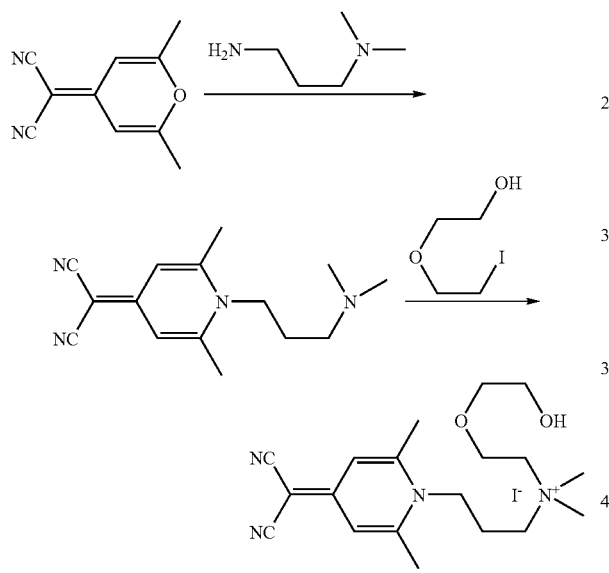

a) 4-dicyanomethylene-2,6-dimethyl-1,4-dihydropyridine-N-(3-[N,N-dimethylamino]-propane)

A 250 ml three necked reaction flask, equipped with a thermometer, a reflux condenser and an oil bath with a magnetic stirrer was charged with 14.5 g (82.2 mmol) of 4-dicyanomethylene-4H-pyran (prepared according *Helv. Chim. Acta* 1962, 1908-1917) and 10.1 g (99 mmol) of 3-(N,N-dimethylamino)-propylamine (Fluka) in 145 ml of n-butanol and heated for two hours under Ar atmosphere. After cooling the suspension was filtered the filter residue was washed with cold n-butanol, to yield after drying 10.4 g of slightly yellowish crystals. M.p. 187-188° C. UV(ethanol) 360 nm (37'287).

b) 2-[2-(2-iodoethoxy)-ethoxy]-ethanol

A 25 ml reaction flask, equipped with a reflux condenser, an oil bath and a magnetic stirrer was charged with 2 g (11.9 mmol) of 2-[2-(2-chloroethoxy)-ethoxy]-ethanol (Fluka), 4 g of sodium iodide and 3 g of sodium hydrogencarbonate in 20 ml of Acetone. The reaction mixture is refluxed over night and when cold, filtered. The filtrate is concentrated at the rotavap, dissolved in 5 ml of $CH_2Cl_2$ and filtered again. Then the filtrate is concentrated again at the rotavap to yield 2.5 g of a yellow oil. The NMR shows a pure substance ($CDCl_3$) 2.58 s broad (1H/OH); 3.22 t (2H/$CH_2$-J); 3.53-3.77 m (10H/$CH_2$—O).

c) 4-dicyanomethylene-2,6-dimethyl-1,4-dihydropyridine-N-[3-(N,N-dimethyl-N-(ethoxy-ethoxy ethanol-yl)-propyl-ammonium iodide]

A 50 ml reaction flask, equipped with a reflux condenser, an oil bath and a magnetic stirrer was charged with 1.28 g (5 mmol) of the above prepared 4-dicyanomethylene-2,6-dimethyl-1,4-dihydropyridine-N-(3-[N,N-dimethylamino]-propane), 1.34 g (5.5 mmol) of the above described 2-[2-(2-iodoethoxy)-ethoxy]-ethanol in 15 ml of DMF. The reaction mixture is refluxed over night and shows no starting material by TLC. The reaction mixture was concentrated at the rotavap, followed by HV drying. The residue is washed with cyclohexane and then with ethylacetate followed by recrystallization from ethanol. Yield 2.09 g of brown crystals. M.p. 130-180° C. decomp.; UV(ethanol) 362 nm (37'946).

EXAMPLE 4

1-{2-[2-(4-dicyanomethylene-2,6-dimethyl-4H-pyridin-1-yl)-ethoxy]-ethyl}-pyridinium chloride

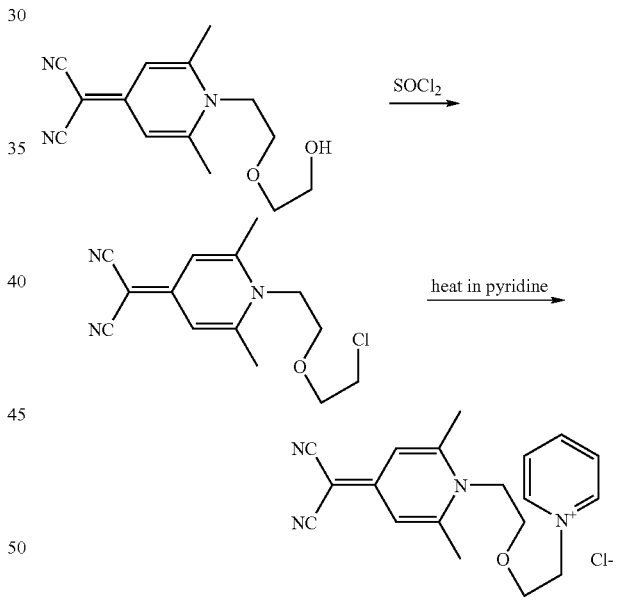

a) 2-{1-[2-(2-chloro-ethoxy)-ethyl]-2,6-dimethyl-1H-pyridin-4-ylidene}-malononitrile A 750 ml four necked reaction flask, equipped with a thermometer, dropping funnel, a reflux condenser, a cooling and a heating bath with a magnetic stirrer was charged under Argon with 19.5 g (75 mmol) of the above prepared 4-Dicyanomethylene-2,6-dimethyl-1,4-dihydropyridine-N-(etholoxy-ethanol) (Example 6.1.a) and a trace of triethylamine (Fluka) in 250 ml of THF and cooled to 10° C. Then a solution of 10.7 g (90 mmol) of $SOCl_2$ in 50 ml of THF is added by means of the dropping funnel within 15 min. This mixture is stirred for 1 hour at room temperature and then heated to reflux for four hours. The reaction is traced by HPLC. The mixture is poured onto ice, and the product is filtered off and recrystallized from ethylacetate. White crystals were obtained, m.p. 148-149° C.

b) 1-{2-[2-(4-dicyanomethylene-2,6-dimethyl-4H-pyridin-1-yl)-ethoxy]-ethyl}-pyridinium chloride A 50 ml reaction flask, equipped with a reflux condenser, a heating bath and a magnetic stirrer was charged under Argon with 1.4 g (5 mmol) of the above 2-{1-[2-(2-chloro-ethoxy)-ethyl]-2,6-dimethyl-1H-pyridin-4-ylidene}-malononitrile in 25 ml of pyridine and heated to reflux for 5 hours. A heavy suspension was formed, which was filtered off and washed with a small amount of cold pyridine followed by THF. After drying 1.69 g of fine crystals were obtained, m.p. 248-251° C./decomp. UV (water) 352 nm (E=1149). Solubility in water>>200 g/l.

EXAMPLE 5

3-[3-(4-dicyanomethylene-2,6-dimethyl-4H-pyridin-1-yl)-phenoxy]propane-1-sulfonic acid

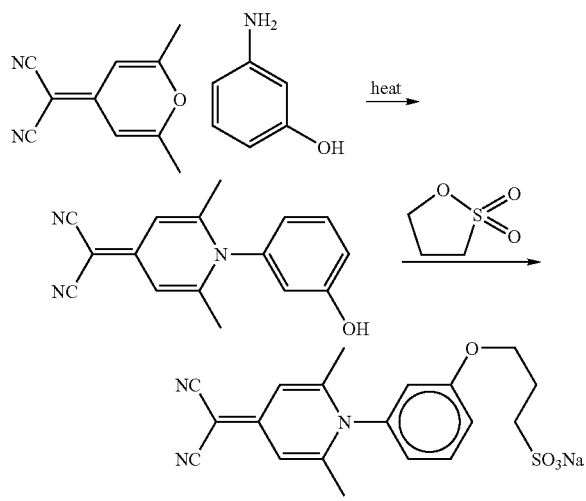

a) 2-[1-(3-hydroxy-phenyl)-2,6-dimethyl-1H-pyridin-4-ylidene]-malononitrile

A 10 ml reaction flask, equipped with a reflux condenser, a magnetic stirrer and an oil bath was charged with 0.86 g (5 mmol) of 4-dicyanomethylene-4H-pyran (prepared according to Helv. Chim. Acta 1962, 1908-1917) and 2.8 g (25 mmol) of 3-aminophenol (Fluka) under Ar atmosphere and heated to 140° C. for 5 hours. Still hot, the mixture was poured onto 100 ml of 2 n HCl and extracted twice with 100 ml of ethylacetate. The combined organic phases were backwashed with 2 n HCl, concentrated at the rotavap and dried. The crystals were washed with warm ethylacetate and MeOH and dried again to yield 460 mg of white crystals. M.p.>300° C., TLC (EtOAc:hexane=1:1 on silicagel) Rf=0.15.

b) 3-[3-(4-dicyanomethylene-2,6-dimethyl-4H-pyridin-1-yl)-phenoxy]-propane-1-sulfonic acid A 50 ml three necked reaction flask, equipped with a thermometer, a reflux condenser, a magnetic stirrer and a heating bath was charged under Argon with 263 mg (1 mmol) of the above 2-[1-(3-hydroxy-phenyl)-2,6-dimethyl-1H-pyridin-4-ylidene]-malononitrile and 26.5 mg (1.05 mmol) of dry NaH (95%) suspended in a mixture of 20 ml of dry THF and 0.1 ml of dry DMF. Hydrogen formation was observed. After 45 min. 134 mg (1.1 mmol) of 1,3-propansultone was added to the suspension, and the reaction mixture was heated to 70° C. for 5 hours and followed by HPLC. When cold, the mixture was filtered, and the residue washed with little THF to yield 260 mg of a white powder. This was recrystallized from MeOH/CH$_2$Cl$_2$, washed with CH$_2$Cl$_2$ and dried to yield 190 mg of colorless crystals m.p. 200° C./decomp. UV (water) 352 nm (E=1150) solubility in water>50 g/l.

EXAMPLE 6

Preparation of a O/W Sunscreen Lotion UV-B and UV-A

Broad-spectrum sunscreen lotion containing 2% of the compound of Example 1.

| % w/w | Compound | Chemical Name |
|---|---|---|
| Part A | | |
| 4 | PARSOL MCX | Ethylhexyl methoxycinnamate |
| 1 | PARSOL 1789 | 4-t-Butyl-4'-methoxy-dibenzoyl-methane |
| 2 | PARSOL 340 | Octocrylene |
| 12 | Cétiol LC | Cocoyl-caprylate caprate |
| 4 | Dermol 185 | Isostearyl neopentanoate |
| 0.25 | PEG-2-stearate | Diethyleneglycol monostearate |
| 1 | Cetylalcohol | Cetylalcohol |
| 0.25 | MPOB/PPOB | Methyl-propylparabene |
| 0.1 | EDTA BD | EDTA-sodium salt |
| 1 | Amphisol DEA (Givaudan) | Diethanolamine cetylphosphate |
| Part B | | |
| 2 | Product of Example 1 | |
| 0.2 | Permulene TR-1 | Acrylate C10-C30 alkylacrylate |
| 66.4 | Water deionized | Water deionized |
| 5 | Propyleneglycol | 1,2-Propanediol |
| 0.8 | KOH (10%) | Potassium hydroxide |

Part A is heated in a reactor to 85° C. Part B is slowly added within 10 minutes, followed by addition of KOH, cooling and degassing of the emulsion.

EXAMPLE 7

| Sun milk waterproofed | | |
|---|---|---|
| % w/w | Ingredient | Chemical Name |
| Part A | | |
| 4 | PARSOL 5000 | 4-Methylbenzylidene camphor |
| 8 | Parsol MCX | Ethylhexyl methoxicinnamate |
| 2 | Uvinul T 150 | Ethylhexyltriazone |
| 1 | Silicone DC 200/350 cs | Dimethicone |
| 2 | Lanette O | Cetylstearyl alcohol |
| 3 | Softisan 100 | Hydrogenated coco-glycerides |
| 6 | Tegosoft TN | C12-15 Alkyl benzoate |
| 7 | Cetiol B | Dibutyl adipate |
| 2 | VITAMIN E ACETATE | Tocopheryl acetate |
| 1 | Berkemyol (Grape Seed) | Palmitoyl Grape seed Extract |
| 0.05 | BHT | Butylhydroxytoluol |

-continued

| Sun milk waterproofed | | | |
|---|---|---|---|
| % w/w | Ingredient | Chemical Name | |
| 0.10 | Edeta BD | Disodium EDTA | |
| 0.60 | Phenonip | Phenoxyethanol & Methylparaben & Ethylparaben & Propylparaben & Butylparaben | |
| 2 | AMPHISOL | Cetyl phosphate DEA | |
| Part B | | | |
| ad 100 | Water deionized | Water deionized | |
| 3 | Product of Example 2 | | |
| 5 | Propylene Glycol | Propylene glycol | |
| 0.30 | Carbopol 980 | Carbomer | |
| Part C | | | |
| 1.5 | KOH (10% sol.) | Potassium Hydroxide | |

EXAMPLE 8

| Sprayable Sunscreen lotion | | | | |
|---|---|---|---|---|
| | Ingredients | INCI Nomenclature | | % w/w |
| A) | PARSOL MCX | Ethylhexyl Methoxycinnamate | 1) | 6.00 |
| | PARSOL 5000 | 4-Methylbenzylidene Camphor | 1) | 2.00 |
| | Emulgade SE-PF | Glyceryl Stearate (and) Ceteareth-20 (and) Ceteareth-12 (and) Cetearyl Alcohol (and) Cetyl Palmitate | 2) | 7.00 |
| | Eumulgin B-2 | Ceteareth-20 | 2) | 6.00 |
| | Myritol 318 | Caprylic/Capric Triglyceride | 2) | 3.00 |
| | Cetiol A | Hexyl Laurate | 2) | 6.00 |
| | Silicone DC 345 fluid | Cyclomethicone | 6) | 7.00 |
| | Antaron V-220 | PVP/Eicosene Copolymer | 7) | 2.00 |
| | Edeta BD | Disodium EDTA | 3) | 0.10 |
| | Butylated Hydroxytoluene | BHT | 5) | 0.05 |
| | Phenonip | Phenoxyethanol & Methylparaben & Ethylparaben & Propylparaben & Butylparaben | 8) | 0.60 |
| B) | Water deionized | Aqua | | q.s. 100 |
| | Glycerine | Glycerin | 5) | 5.00 |
| C) | PARSOL HS | Phenylbenzimidazole Sulfonic Acid | 1) | 2.00 |
| | Product of Example 2 | | | 2.00 |
| | Water deionized | Aqua | | 20.00 |
| | KOH 10% sol. | Potassium Hydroxide | | 4.40 |

Procedure:

Heat part A) to 85° C. while stirring. When homogeneous, add part B) (80° C.) under stirring. Then add part C) (40° C.) while stirring (be sure that Parsol HS has been completely dissolved, if traces remain, add a small quantity of the neutralizing base until the solution is clear pH>7). Finally adjust the pH to a minimum of 7.0, and cool to RT.

Suppliers:

1) DSM Nutritional Products, CH-4002 Basel/Switzerland

2) COGNIS, D-40551 Düsseldorf/Germany

3) BASF AG, D-67056 Ludwigshafen/Germany

4) GOODRICH COMPANY, Cleveland-Ohio 44141-3247/USA

5) FLUKA CHEMIE AG, CH-9471 Buchs/Switzerland

6) DOW CORNING CORP., Midland-Mich. 48686-0994/USA

7) ISP TECHNOLOGIES INC., Wayne-N.J. 07470/USA

8) NIPA LABORATORIES LTD, Mid Glam.-CF38 2SN/England

EXAMPLE 9

| O/W VITAMINIZED BROAD SPECTRUM SUNSCREEN LOTION | | | | |
|---|---|---|---|---|
| | Ingredients | INCI Nomenclature | | % w/w |
| A) | PARSOL MCX | Ethylhexyl Methoxycinnamate | 1) | 4.00 |
| | PARSOL 1789 | Butyl Methoxydibenzoylmethane | 1) | 1.00 |
| | PARSOL 5000 | 4-Methylbenzilidene Camphor | 1) | 3.50 |
| | Estol GMM 3650 | Glyceryl Myristate | 8) | 4.00 |
| | Cetyl Alcohol | Cetyl Alcohol | | 2.00 |
| | Ganex V-220 | PVP/Eicosene Copolymer | 4) | 2.00 |
| | Tegosoft TN | C12-15 Alkyl Benzoate | 5) | 10.00 |
| | Myritol 318 | Caprylic/Capric Triglyceride | 6) | 6.00 |
| | Butylated Hydroxytoluene | BHT | | 0.05 |
| | Edeta BD | Disodium EDTA | 2) | 0.10 |
| | Phenonip | Phenoxyethanol & Methylparaben & Ethylparaben & Propylparaben & Butylparaben | 3) | 0.60 |
| | AMPHISOL K | Potassium Cetyl Phosphate | 1) | 2.00 |
| | VITAMIN E ACETATE | Tocopheryl Acetate | 1) | 2.00 |
| B) | Water deionized | Aqua | | ad 100 |
| | Propylene Glycol | Propylene Glycol | | 5.00 |
| | Carbopol 981 (1% sol.) | Carbomer | 7) | 10.00 |
| | D-PANTHENOL 75L | Panthenol | 1) | 2.70 |
| C) | KOH (10% sol.) | Potassium Hydroxide | | 0.70 |
| D) | Water deionized | Aqua | | 20.00 |
| | Product of Example 2 | | | 2.00 |
| | PARSOL HS | Phenylbenzimidazole Sulfonic Acid | 1) | 2.00 |
| | KOH (10% sol.) | Potassium Hydroxide | | 4.00 |

Procedure:

Heat part A) to 85° C. while stirring. When homogeneous, add part B) and C) pre-heated to 75° C. under agitation. Add part D) pre-heated to 75° C. (be sure that PARSOL HS has completely dissolved, if traces remain, add a small quantity of the neutralizing base until the solution is clear). Homogenize at 11000 rpm for 30 sec. Cool to room temperature.

Physical Data:

pH: 7.20

Viscosity (Brookfield RVT, 25° C., spindle 6, 10 rpm): approx. 12350 cP

SPF: in vivo determination according Colipa protocol, 5 subjects, Laboratoire Dermscan, Lyon Ref.98098 (02.98)

Suppliers:

9) ROCHE VITAMINS LTD, CH-4070 Basel/Switzerland

10) BASF AG, D-67056 Ludwigshafen/Germany

11) NIPA LABORATORIES LTD, Mid Glam.-CF38 2SN/England

12) ISP TECHNOLOGIES INC., Wayne-N.J. 07470/USA
13) GOLDSCHMIDT AG, D-45127/Germany
14) COGNIS, D-40551 Düsseldorf/Germany
15) B.F. GOODRICH COMPANY; Cleveland-Ohio44141/USA
16) UNICHEMA CHEMIE GmbH, D-46446 Emmerich/Germany
The invention claimed is:
1. A compound which is selected from the group consisting of:
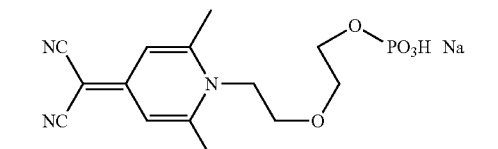
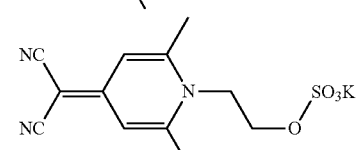
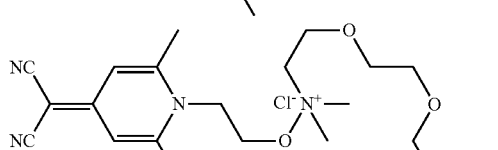
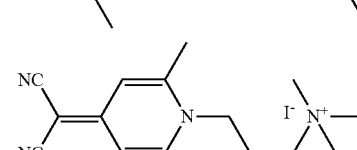
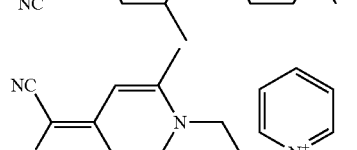
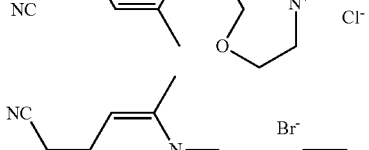
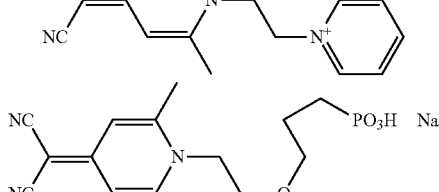
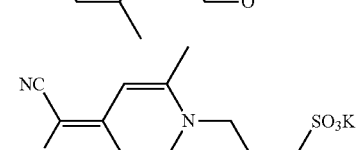
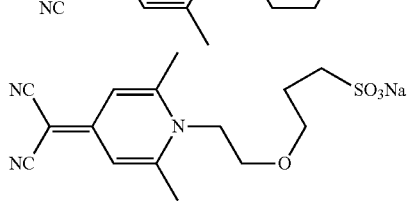
-continued
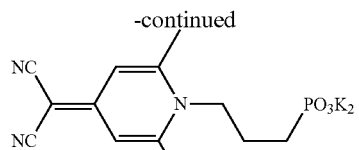
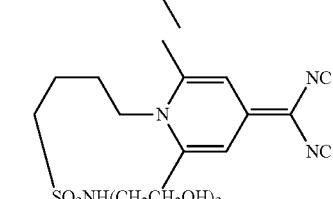
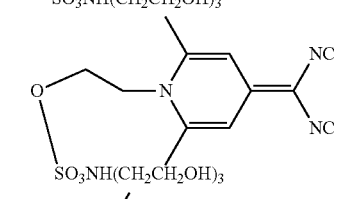
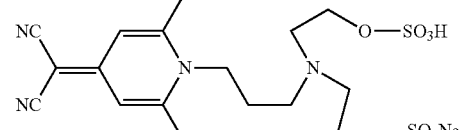
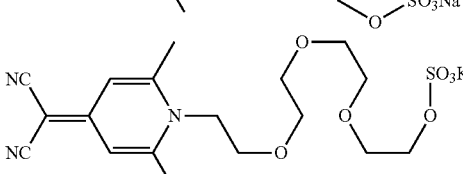
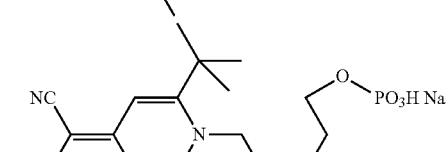
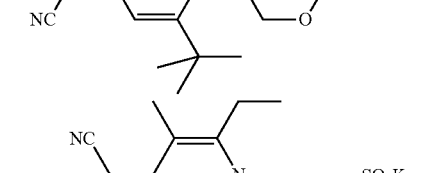
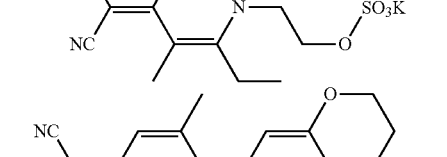
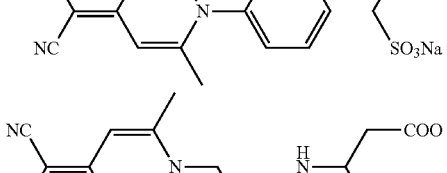
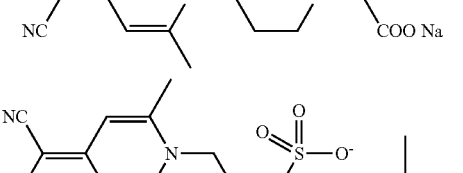
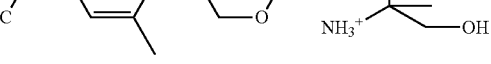

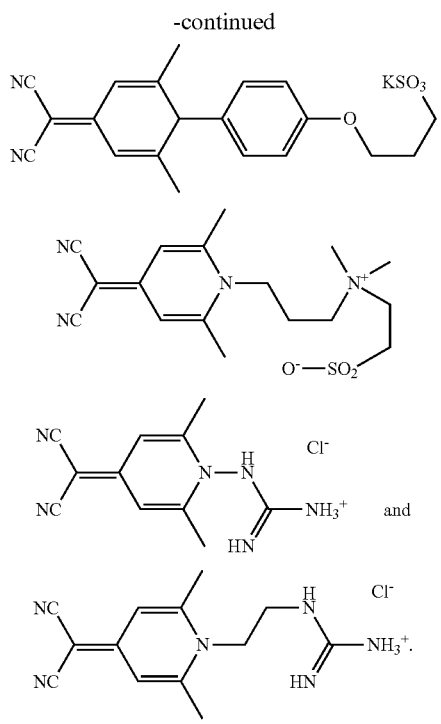
2. The compound according to claim 1, wherein the compound is selected from the group consisting of:
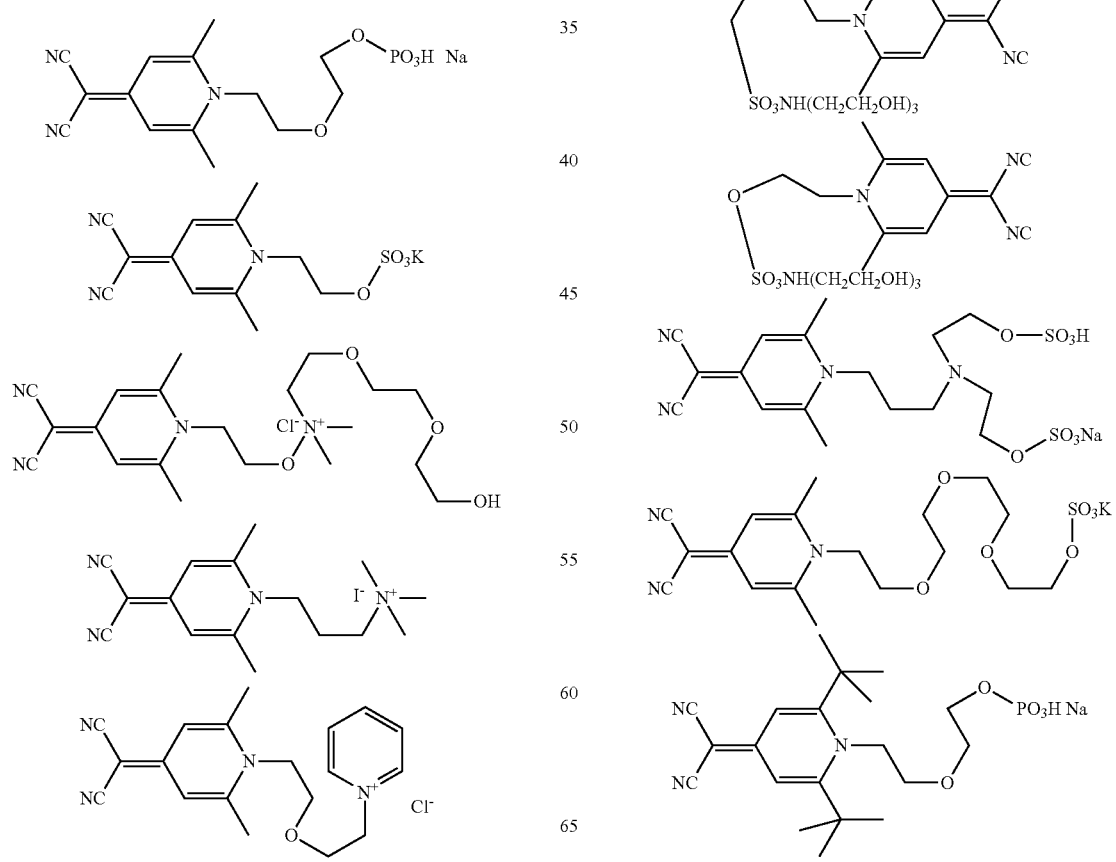

-continued
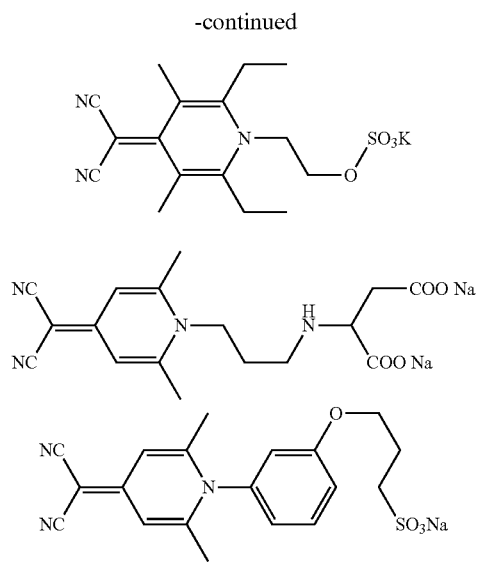
-continued
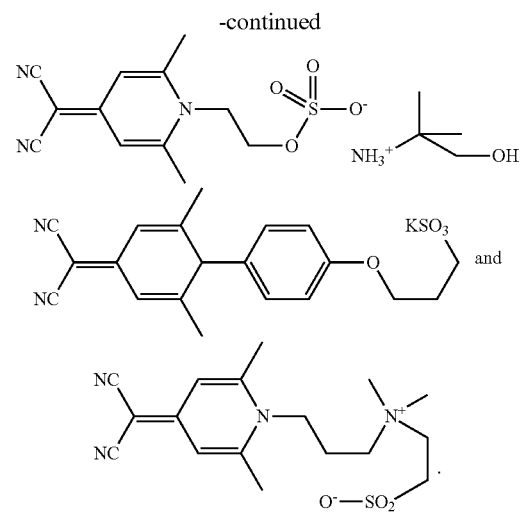
* * * * *